United States Patent [19]

Lucy et al.

[11] Patent Number: 4,816,595

[45] Date of Patent: Mar. 28, 1989

[54] PREPARATION OF CARBONATE ESTERS

[75] Inventors: Andrew R. Lucy, Camberley; George E. Morris, Egham, both of England

[73] Assignee: British Petroleum Company p.l.c., London, England

[21] Appl. No.: 918,138

[22] Filed: Oct. 14, 1986

[30] Foreign Application Priority Data

Oct. 24, 1985 [GB] United Kingdom ............... 8526306

[51] Int. Cl.$^4$ ...................... C07C 68/00; C07C 69/96
[52] U.S. Cl. ..................................... 558/277; 558/260
[58] Field of Search ............................... 558/260, 277

[56] References Cited

U.S. PATENT DOCUMENTS 3,114,762  12/1963  Mador et al. .................. 558/277 X

FOREIGN PATENT DOCUMENTS 112171  6/1984  European Pat. Off. ............ 558/277
112172  6/1984  European Pat. Off. ............ 558/277

*Primary Examiner*—Vivian Garner
*Attorney, Agent, or Firm*—Nixon & Vanderhye

[57] ABSTRACT

A process for preparing carbonate esters by the oxidative carbonylation of an alcohol is provided. The process comprises reacting an alcohol with carbon monoxide in the presence of a dihydrocarbyl peroxide the process being characterized by the fact that the carbon monoxide pressure at the reaction temperature is less than 15 bars and by the fact that a catalyst comprising a platinum group metal and a copper compound is employed. The process is useful for preparing dimethyl carbonate from methanol and carbon monoxide.

12 Claims, No Drawings

PREPARATION OF CARBONATE ESTERS

The present invention relates to the preparation of esters of carbonic acid also known as carbonate esters. In particular the present invention relates to the preparation of carbonate esters by reacting an alcohol with carbon monoxide in the presence of a dihydrocarbyl peroxide and a catalyst.

Carbonate esters are useful as solvents, chemical intermediates and potential gasoline additives.

Our European patent application EP No. 112172 discloses a process for the preparation of a carbonate ester by reacting a primary or secondary alcohol with carbon monoxide in the presence of a dihydrocarbyl peroxide using a copper catalyst. In this application high yields of carbonate ester are produced by carrying out the process at a carbon monoxide pressure in the range 15 to 50 bar.

Our other European patent application EP No. 112171 teaches the formation of esters of oxalic acid by reacting an alcohol with carbon monoxide in the presence of a dihydrocarbyl peroxide using a platinum group metal and copper catalyst. In this application the carbon monoxide pressure is suitably greater than 15 bar. Example 4 of this patent teaches that carbonate byproduct can be prepared at a pressure of 33 bar albeit in low yield.

It has now been discovered that, by operating at a pressure below 15 bar, carbonate esters can be selectively produced in good yields at a high reaction rate by reacting an alcohol with carbon monoxide in the presence of a dihydrocarbyl peroxide, using a platinum group metal and copper catalyst. Under these conditions the carbonate ester is obtained as the major product and the oxalate ester as a byproduct.

In addition it has been discovered that the yields, selectivities and reaction rates obtained with such a catalyst can be further improved by using a promoter selected from (1) a heterocyclic, aromatic nitrogen containing compound, (2) a nitrile or (3) a Group IA or IIA halide salt or a mixture of at least two of these promoters.

Accordingly, the present invention provides a process for the preparation of an ester of carbonic acid which process comprises reacting an alcohol with carbon monoxide in the presence of a dihydrocarbyl peroxide characterised in that the pressure of carbon monoxide, at the temperature at which the process is operated, is less than 15 bar and that the process is carried out in the presence of an effective amount of catalyst comprising a platinum group metal and a copper compound.

The ester of carbonic acid which is produced comprises carbonic acid esterified with two molecules of the alcohol.

As regards the alcohol used in the process, it can, in principle, be any alcohol including both monofunctional and polyfunctional alcohols. Suitably the alcohol used is a $C_1$ to $C_{20}$ aliphatic or cycloaliphatic alcohol, e.g. a $C_1$ to $C_{12}$ alcohol, of which $C_1$ to C primary, secondary or tertiary aliphatic alcohols are preferred. Examples of preferred alcohols include methanol, ethanol, 1-propanol, 2-propanol, 1-butanol, 2-butanol and tertiary butanol. The alcohol may be added to the reaction mixture as such or may be generated in situ by the decomposition of the dihydrocarbyl peroxide. Thus, if the dihydrocarbyl peroxide used is di-tertiary butyl peroxide, it is possible to carry out the process in the absence of deliberately added alcohols by using the tertiary butanol, or some chemical intermediate derived from it, produced by the decomposition of the peroxide under the reaction conditions. It will be appreciated that such a reaction will occur even when an alcohol is deliberately added as there will always be produced such alcohols or intermediates. Hence in most cases more than one type of carbonate ester will appear in the product.

Carbon monoxide is available commercially on a large scale for example as a product of the steam reforming of methane or by partial oxidation of hydrocarbons. The carbon monoxide can be used substantially pure or with small amounts (e.g. less than 10% by volume) of impurities such as hydrogen, carbon dioxide and nitrogen.

The process of the present invention is operated so that, at the temperature at which the reaction is carried out, the pressure of carbon monoxide is less than 15 bar. Preferably the pressure used is in the range 5 to 10 bar for primary and secondary alcohols and 2 to 5 bar for tertiary alcohols. When choosing the pressure it should be remembered that, in general, increasing pressure causes an increase in reactivity but a decrease in reaction selectivity. The final choice of operating will therefore be dictated by considerations such as whether it is desired to make and sell the side-products.

With regard to the dihydrocarbyl peroxide, the hydrocarbyl radical may suitably be an alkyl, aryl, alkaryl or aralkyl group having up to 9 carbon atoms. The two hydrocarbyl radicals present in the dihydrocarbyl peroxide may be the same or different. The hydrocarbyl peroxide may have the formula $(R\ R^1\ R^2)C-O-O-C(R\ R^1\ R^2)$ where $R, R^1$ and $R^2$ are independently hydrogen or hydrocarbyl radicals selected from the group consisting of alkyl, aryl or aralkyl having up to nine carbon atoms. The dihydrocarbyl peroxide, is preferably either di-cumyl peroxide, or di-tertiary-butyl peroxide (DTBP). DTBP may readily be obtained, for example, by reacting tertiary-butyl alcohol with tertiary-butyl hydroperoxide, which in turn may readily be obtained by oxidation of isobutene. A suitable process for producing DTBP is described in US Patent No 2862973. Dicumyl peroxide may be prepared from cumene by partial oxidation. Conveniently, the dihydrocarbyl peroxide is added in amounts such that the molar ratio of dihydrocarbyl peroxide to alcohol lies in the range 10,000:1 to 1:100, preferably 5:1 to 1:5.

With regard to the catalyst, this contains both a platinum group metal and a copper compound. The platinum group metal can be palladium, platinum, rhodium, ruthenium, osmium or iridium in elemental or compound form. Preferably the platinum group metal is palladium. The platinum group metal can be added as a simple inorganic salt e.g. halide, nitrate, sulphate and the like, an organic salt e.g. an acetate or acetoacetonate or a complex salt such as an amine or phosphine complex.

The copper compound is conveniently a copper (1) salt (i.e. a cuprous salt) and is preferably a halide, for example copper (1) chloride or copper (1) bromide or a copper (II) alkoxide e.g. copper methoxy pyridine chloride.

The platinum group metal/copper catalyst is added in amounts less than 10% by weight of the reactor charge. Preferably the molar ratio of platinum group metal to copper compound in the catalyst should be in the range 5:1 to 1:200 preferably 1:1 to 1:20.

In addition to the platinum group metal/copper catalyst described above a promoter may be used. The promoter is suitably one or more members of the three classes of compounds comprising (1) heterocyclic aromatic nitrogen containing compounds, (b) nitriles or (c) Group IA or IIA halide salts.

As regards the heterocyclic aromatic nitrogen compound this is preferably one containing a trivalent nitrogen atom. Examples of such compounds include pyridines, pyrroles, imidazoles, N-methylimidazoles, quinolines and the like. Most preferably the heterocyclic aromatic nitrogen containing compound is pyridine or a substituted derivative such as an alkylpyridine or a dialkylpyridine e.g. 2,6-dimethylpyridine.

The nitrile promoters which form the second class of promoters can be any organic molecule containing one or more cyanide groups. This class includes alkyl, cycloalkyl and aryl nitriles. Preferably the nitrile is a $C_1$–$C_{12}$ alkyl nitrile having one or more cyanide groups, for example acetonitrile, propionitrile or adiponitrile, or an aromatic nitrile, e.g. benzonitrile.

The final group of promoters consists of Group IA or IIA halide salts suitably those which are soluble in the reaction medium. Preferably the salt is either lithium chloride or lithium bromide.

The molar ratio of promoter to copper compound is suitably in the range 1:20 to 1000:1 preferably 1:1 to 100:1.

It is convenient to carry out the reaction at temperatures in excess of ambient. Although the specific temperature used will depend to a certain extent upon the exact nature of the reactants, the reaction is generally carried out at a temperature in the range 30 to 120° C. preferably in the range 50° to 110° C.

The reaction is generally carried out in the liquid phase using the reactants as a medium for the reaction. An inert solvent such as tetrahydrofuran or an acetamide can however be used if desired.

It is possible to operate such a process as described above both batchwise or continuously.

After the process is carried out the ester of the carbonic acid may be separated from the product mixture by for example distillation.

The invention described herein will now be illustrated by the following examples.

EXAMPLE 1

A 150 ml stainless steel autoclave was charged with 15.2g of ditertiary butyl peroxide (DTBP), 7.05g of methanol, 0.14g of cuprous chloride and 0.024g of palladium dichloride. The autoclave was sealed and pressurised with carbon monoxide and heated to a temperature of 90° C. During the heat up period the pressure of carbon monoxide was adjusted so that at the working temperature the total pressure was 5 bar (equivalent to ca 4.5 bar partial pressure of carbon monoxide). After 15 hours, the autoclave was cooled, depressurised and emptied. The liquid contents were analysed by GLC and the weight of dimethyl carbonate (DMC) produced calculated.

Comparative Test A

Example 1 was repeated except that the palladium dichloride was omitted and rum time was 16 hours.

EXAMPLE 2

Example 1 was repeated except that 0.33g of lithium chloride was also added. In this Example, the run time was 4 hours.

EXAMPLE 3

Example 2 was repeated except that the lithium chloride was replaced by 4.2g of benzonitrile.

EXAMPLE 4

Example 1 was repeated except hat 3.23g of pyridine was also added.

EXAMPLE 5

Example 4 was repeated except that the reaction time was eight hours and 0.33g of lithium chloride was added.

EXAMPLE 6

Example 3 was repeated except that 0.33 g of lithium chloride was also added.

The results of all Examples and the Comparative Test are given in the Table.

EXAMPLE 7

A stainless steel autoclave of 150 ml internal volume, fitted with a magnetic follower, was charged with 15g of di-tertiary-butyl peroxide, 7g of tertiary butanol, 4g of benzonitrile, 0.34g of lithium chloride, 0.14g of cuprous chloride and 0.025 g of palladium dichloride. The vessel was pressurized with carbon monoxide and connected to a carbon monoxide reservoir set to maintain the reactor pressure at three bar gauge (ca 3.5 bar partial pressure of CO). The vessel was heated with stirring to 90° C., maintained at that temperature for 2.75 hours, then allowed to cool. The product was found to contain 1 g of di-tertiary-butyl peroxide, 13.8g of di-tertiary-butyl carbonate and 0.2g of di-tertiary-butyl oxalate.

Comparative Test B

Example 7 was repeated with 0.3g of cuprous chloride and in the absence of palladium dichloride. The temperature was maintained at 90° C. for 18 hours, gas uptake ceasing after 10 hours. The product was found to contain 0.9g of di-tertiary-butyl peroxide, 6.3g of di-tertiary-butyl carbonate and 0.1g of di-tertiary-butyl oxalate.

EXAMPLE 8

Example 7 was repeated with 0.25g of cuprous chloride and 0.001g of palladium dichloride. The reactor was held at 90° C. for 2 hours and the pressure at 11.5 bar gauge (ca 11 bar partial pressure of CO). The product was found to contain 1.5g of di-tertiary-butyl peroxide, 3.9g of di-tertiary-butyl carbonate and 9.5g of di-tertiary-butyl oxalate.

EXAMPLE 9

Example 8 was repeated with the reactor pressure being maintained at a pressure of 3 bar gauge (ca 3.5 bar partial pressure of CO) for 2.5 hours. The initial rate of gas uptake was one third of that observed in Example 9. The product was found to contain 0.6g of di-tertiary butyl peroxide, 10.7g of di-tertiary-butyl carbonate and 3.7g of di-tertiary-butyl oxalate.

TABLE

|  | Example 1 | Comparative Test A | Example 2 | Example 3 | Example 4 | Example 5 | Example 6 |
| --- | --- | --- | --- | --- | --- | --- | --- |
| Run time (hrs) | 15 | 16 | 4 | 4 | 16 | 8 | 4 |
| DTBP Used (g) | 12.9 | 4.0 | 14.2 | 12.5 | 15.3 | 15.0 | 14.3 |
| DMC Produced (g) | 1.7 | 0.04 | 7.7 | 4.0 | 5.2 | 6.05 | 7.1 |
| Rmax | 16.0 | not measured | 63.0 | 32 | 15 | 18 | 47 |
| Selectivity to DMC (Based on DTBP consumed) | 22.0 | 1.00 | 89.0 | 52 | 55.2 | 65 | 81 |

Rmax = initial rate of carbon monoxide uptake expressed as the turnover rate for DMC on copper per hour.

We claim:

1. In a process for the preparation of an ester of carbonic acid which process comprises reacting a $C_1$ to $C_{20}$ aliphatic or cycloaliphatic alcohol with carbon monoxide in the presence of a dihydrocarbyl peroxide, the improvement comprising carrying out the process with the pressure of carbon monoxide at the temperature at which the process is carried out being less than 15 bars and carrying out the process in the presence of a nitrile promoter, a Group IA or IIA halide salt as promoter and an effective amount of a catalyst comprising a platinum group metal and a copper compound.

2. A process as claimed in claim 19, wherein the dihydrocarbyl peroxide has the formula $(RR^1R^2)C-O-O-C(RR^1R^2)$ where R, $R^1$ and $R^2$ are independently hydrogen or hydrocarbyl radicals selected from the group consisting of alkyl, aryl, and aralkyl radicals having up to nine carbon atoms.

3. A process as claimed in claim 20, wherein the dihydrocarbyl peroxide is di-tertiary butyl peroxide or dicumyl peroxide.

4. A process as claimed in claim 19, wherein the platinum group metal is palladium.

5. A process as claimed in claim 19, wherein the copper compound is a copper (1) compound.

6. A process as claimed in claim 19, wherein the alcohol is a $C_1$ to $C_{12}$ aliphatic or cycloaliphatic alcohol.

7. A process as claimed in claim 24, wherein the alcohol is selected from methanol, ethanol, isopropanol, n-butanol and tertiary butanol.

8. A process as claimed in claim 1, wherein the nitrile promoter is benzonitrile.

9. A process as claimed in claim 1, wherein the Group IA or IIA halide promoter is either lithium chloride or lithium bromide.

10. A process as claimed in claim 1, wherein the carbon monoxide pressure is in the range of 5 to 10 bars.

11. A process as claimed in claim 1, wherein the carbon monoxide pressure is in the range of 2 to 5 bars.

12. A process according to claim 1, wherein the process is carried out at a temperature in the range of 50 to 110° C.

* * * * *